United States Patent
Yamamoto et al.

(10) Patent No.: US 9,898,815 B2
(45) Date of Patent: Feb. 20, 2018

(54) FAULT DIAGNOSTIC DEVICE OF ROBOT SYSTEM FOR JUDGING FAULT BY CAMERA IMAGE

(71) Applicant: FANUC CORPORATION, Yamanashi (JP)

(72) Inventors: Tomoyuki Yamamoto, Yamanashi (JP); Hiromitsu Takahashi, Yamanashi (JP)

(73) Assignee: FANUC CORPORATION, Yamanashi (JP)

( * ) Notice: Subject to any disclaimer, the term of this patent is extended or adjusted under 35 U.S.C. 154(b) by 0 days.

(21) Appl. No.: 15/426,362

(22) Filed: Feb. 7, 2017

(65) Prior Publication Data
US 2017/0243339 A1    Aug. 24, 2017

(30) Foreign Application Priority Data
Feb. 19, 2016    (JP) .................................. 2016-029635

(51) Int. Cl.
*G06T 7/00*    (2017.01)
*G01N 21/88*    (2006.01)
(Continued)

(52) U.S. Cl.
CPC ............ *G06T 7/001* (2013.01); *B25J 9/0084* (2013.01); *B25J 9/1674* (2013.01); *B25J 19/023* (2013.01);
(Continued)

(58) Field of Classification Search
None
See application file for complete search history.

(56) References Cited

U.S. PATENT DOCUMENTS 6,882,962 B2    4/2005    Aoyama
7,177,459 B1 *  2/2007    Watanabe .............. B25J 9/1697
                                                              382/151
(Continued)

FOREIGN PATENT DOCUMENTS

CN    101115988 A    1/2008
DE    102014203798 A1    9/2015
(Continued)

OTHER PUBLICATIONS

AL Christensen, "Fault Detection in Autonomous Robots," PhD Dissertation, Université Libre de Bruxelles, 2008.*
(Continued)

*Primary Examiner* — Vikkram Bali
*Assistant Examiner* — Soo Shin
(74) *Attorney, Agent, or Firm* — Hauptman Ham, LLP (57) ABSTRACT

A fault diagnostic device comprises an arithmetic processing device configured to judge a fault on the basis of an image captured by the camera. The arithmetic processing device includes an imaging command part configured to transmit a command for capturing the image of a diagnosis portion and a judgement part configured to judge whether or not the diagnosis portion has the fault. A storage part stores a reference image when the diagnosis portion is in a normal state. The imaging command part transmits an imaging command so as to capture the image of the diagnosis portion after changing a position and a posture of the robot. The judgement part compares the image of the diagnosis portion captured by the camera with the reference image and judges the fault in the diagnosis portion.

7 Claims, 4 Drawing Sheets

(51) Int. Cl.
*B25J 9/00* (2006.01)
*B25J 19/02* (2006.01)
*B25J 9/16* (2006.01)

(52) U.S. Cl.
CPC .............. *G01N 21/8851* (2013.01); *G06T 2207/30108* (2013.01)

(56) References Cited

U.S. PATENT DOCUMENTS

| | | | | |
|---|---|---|---|---|
| 7,400,760 | B2* | 7/2008 | Takizawa | G06K 9/6203 382/153 |
| 2013/0211782 | A1* | 8/2013 | Rosenberg | B25J 9/16 702/182 |
| 2013/0245821 | A1* | 9/2013 | Nakamura | B25J 19/06 700/245 |
| 2014/0379129 | A1* | 12/2014 | Edsinger | B25J 9/0009 700/254 |
| 2015/0254827 | A1* | 9/2015 | Kobayashi | G06T 7/001 348/130 |
| 2015/0332463 | A1* | 11/2015 | Galera | G06K 9/00771 382/103 |
| 2016/0086343 | A1* | 3/2016 | Namiki | G06T 7/593 348/135 |

FOREIGN PATENT DOCUMENTS

| | | |
|---|---|---|
| DE | 102016003316 A1 | 9/2016 |
| DE | 102016008987 A1 | 2/2017 |
| EP | 1882922 B1 | 3/2012 |
| JP | 61-226289 A | 10/1986 |
| JP | 3-289310 A | 12/1991 |
| JP | 9-212219 A | 8/1997 |
| JP | 10-294933 A | 11/1998 |
| JP | 4112594 B2 | 7/2008 |
| JP | 2011-110629 A | 6/2011 |
| JP | 2015-85406 A | 5/2015 |
| KR | 10-2014-0079621 A | 6/2014 |

OTHER PUBLICATIONS

JY Kim, et al., "Fault Management of Robot Software Components based on OPRoS," 2011, 14th IEEE International Symposium on Object/Component/Service-Oriented Real-Time Distributed Computing.*

* cited by examiner

FAULT DIAGNOSTIC DEVICE OF ROBOT SYSTEM FOR JUDGING FAULT BY CAMERA IMAGE

RELATED APPLICATIONS

The present application claims priority to Japanese Patent Application No. 2016-029635 filed Feb. 19, 2016, the disclosure of which is hereby incorporated by reference herein in its entirety.

BACKGROUND OF THE INVENTION

1. Field of the Invention

The present invention relates to a fault diagnostic device of a robot system comprising a robot.

2. Description of the Related Art

It is conventionally known that a manufacturing machine comprising a robot performs an operation such as machining of an article in a manufacturing factory. The manufacturing machine may break down due to long-term use and failure of a component in some cases. For example, the robot includes a movable part such as an arm. The movable part is deteriorated in the long-term use. Accordingly, it is known that the manufacturing machine is equipped with a device for diagnosing failure.

Japanese Patent No. 4112594 discloses an abnormality diagnostic method for diagnosing an abnormality in a reducer of a robot. It is disclosed that the abnormality diagnostic method diagnoses a fault in the reducer on the basis of a torque command and speed feedback to a motor driving the robot.

SUMMARY OF THE INVENTION

The fault of the robot may include the fault of the component arranged inside the robot and the fault of the component arranged outside the robot as well. For example, a power cable for supplying power to an end effector or a communication line for transmitting a signal is arranged on the outside of the arm of the robot in some cases. When the manufacturing machine is used in the long term, the power cable, the communication line, and the like may be corroded.

Alternatively, the robot comes into contact with the other device, whereby the component arranged on the outside may be broken. For example, when the robot comes into contact with the other device, a cover of the arm or a cover of the hand may be damaged. The external damage of the component arranged on the robot cannot be accurately recognized from the signal of a detector in some cases.

A fault diagnostic device of the present invention is the fault diagnostic device of a robot system including a robot. The fault diagnostic device comprises a camera fixed to a distal end of the robot or a work tool attached to the robot. The fault diagnostic device comprises an arithmetic processing device configured to judge a fault in at least one of the robot supporting the camera and a peripheral device around the robot on the basis of an image captured by the camera. The arithmetic processing device includes a storage part configured to store information of a diagnosis portion in which fault judgement is performed and an imaging command part configured to transmit a command for capturing the image of the diagnosis portion. The arithmetic processing device includes a judgement part configured to judge whether or not the diagnosis portion has the fault on the basis of the image captured by the camera. The storage part stores a position and a posture of the robot when the diagnosis portion is imaged and a reference image when the diagnosis portion is in a normal state. The imaging command part transmits an imaging command so as to capture the image of the diagnosis portion by the camera after changing the position and the posture of the robot on the basis of the information of the diagnosis portion. The judgement part compares the image of the diagnosis portion captured by the camera with the reference image and judges that the diagnosis portion has the fault when there is a difference of shapes exceeding a predetermined judgement amount.

In the above-described invention, the storage part can store the reference images of a plurality of diagnosis portions. The imaging command part can transmit the imaging command so as to capture images of the plurality of diagnosis portions. The judgement part can judge the fault in the plurality of diagnosis portions on the basis of the reference images of the plurality of diagnosis portions and the images of the plurality of diagnosis portions captured by the camera.

In the above-described invention, the robot system can comprise a plurality of the robots. The cameras can be attached to the respective robots. The arithmetic processing device can be connected to control devices of the respective robots via a network. The imaging command part can transmit imaging commands to the control devices of the plurality of the robots so as to capture images of a same diagnosis portion from directions different from each other. The arithmetic processing device can acquire the images of the diagnosis portion captured by the respective cameras via the network and judge whether or not the diagnosis portion has the fault.

In the above-described invention, the robot system can comprise a management device connected to the arithmetic processing device via the network, and when the judgement part judges that the diagnosis portion has the fault, the arithmetic processing device can transmit a signal indicating occurrence of the fault in the diagnosis portion to the management device.

In the above-described invention, when the judgement part judges that the diagnosis portion has the fault, the arithmetic processing device can transmit the image of the diagnosis portion to the management device via the network.

In the above-described invention, the arithmetic processing device can include a fault estimation part configured to estimate a portion having a possibility of the fault on the basis of an operation state of the robot. The imaging command part can transmit the imaging command so as to capture the image of the portion which has been judged to have the possibility of the fault by the fault estimation part. The judgement part can judge whether or not the portion which has been judged to have the possibility of the fault has the fault.

In the above-described invention, the arithmetic processing device can include a fault estimation part configured to estimate a portion having a possibility of the fault on the basis of an operation state of the robot. The imaging command part can select the robot capable of capturing the image of the portion which has been judged to have the possibility of the fault by the fault estimation part and transmit the imaging command so as to capture the image of the portion by the camera attached to the selected robot. The judgement part can judge whether or not the portion which has been judged to have the possibility of the fault has the fault.

In the above-described invention, the operation state can include feedback information based on an output of a rotation position detector attached to a motor for driving the robot.

DETAILED DESCRIPTION

A fault diagnostic device of a robot system in an embodiment is described with reference to FIG. 1 to FIG. 5. The fault diagnostic device of the present embodiment captures an image of a robot and a peripheral device arranged around the robot by a camera and judges a fault on the basis of the captured image.

Figure 1:
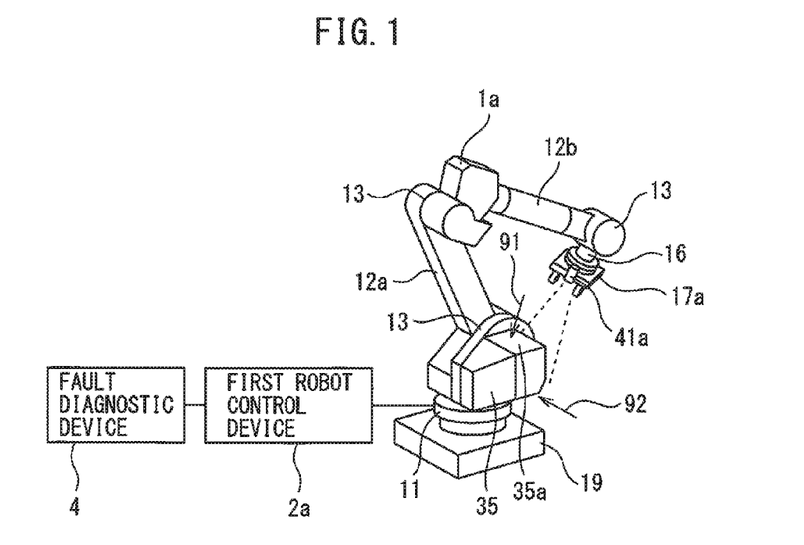
FIG. 1 is a schematic perspective view of a robot of first robot system in an embodiment.

FIG. 1 is a schematic drawing of first robot system in the present embodiment. The first robot system comprises first manufacturing machine and the fault diagnostic device 4. The first manufacturing machine comprises first work tool 17a for performing a predetermined operation and first robot 1a for changing a position and a posture of the work tool 17a. The robot 1a of the present embodiment is an articulated robot including arms 12a and 12b, a wrist portion 16, and a plurality of joint portions 13. The robot 1a includes structural members such as a power source box and a cable.

The robot 1a includes a robot drive device for driving the structural member at each of the joint portions 13. The robot drive device includes a motor for driving the structural member at the joint portion 13. When the motor drives, the arms 12a and 12b and the wrist portion 16 can be turned toward desired directions by the joint portions 13. The robot 1a comprises a base portion 19 fixed onto a floor surface and a revolving portion 11 rotating with respect to the base portion 19. The robot drive device includes a motor for driving the revolving portion 11.

The work tool 17a attached to the robot 1a is also referred to as an end effector. The work tool 17a is attached to the wrist portion 16 of the robot 1a. The work tool 17a of the present embodiment is a hand for grasping a workpiece, however, an arbitrary work tool can be coupled to the robot 1a depending on a content of operation without being limited to this embodiment. The work tool 17a includes a tool drive device 18 for driving the work tool 17a. The tool drive device of the present embodiment includes an air pump for driving the work tool 17a by a pneumatic pressure.

Figure 2:
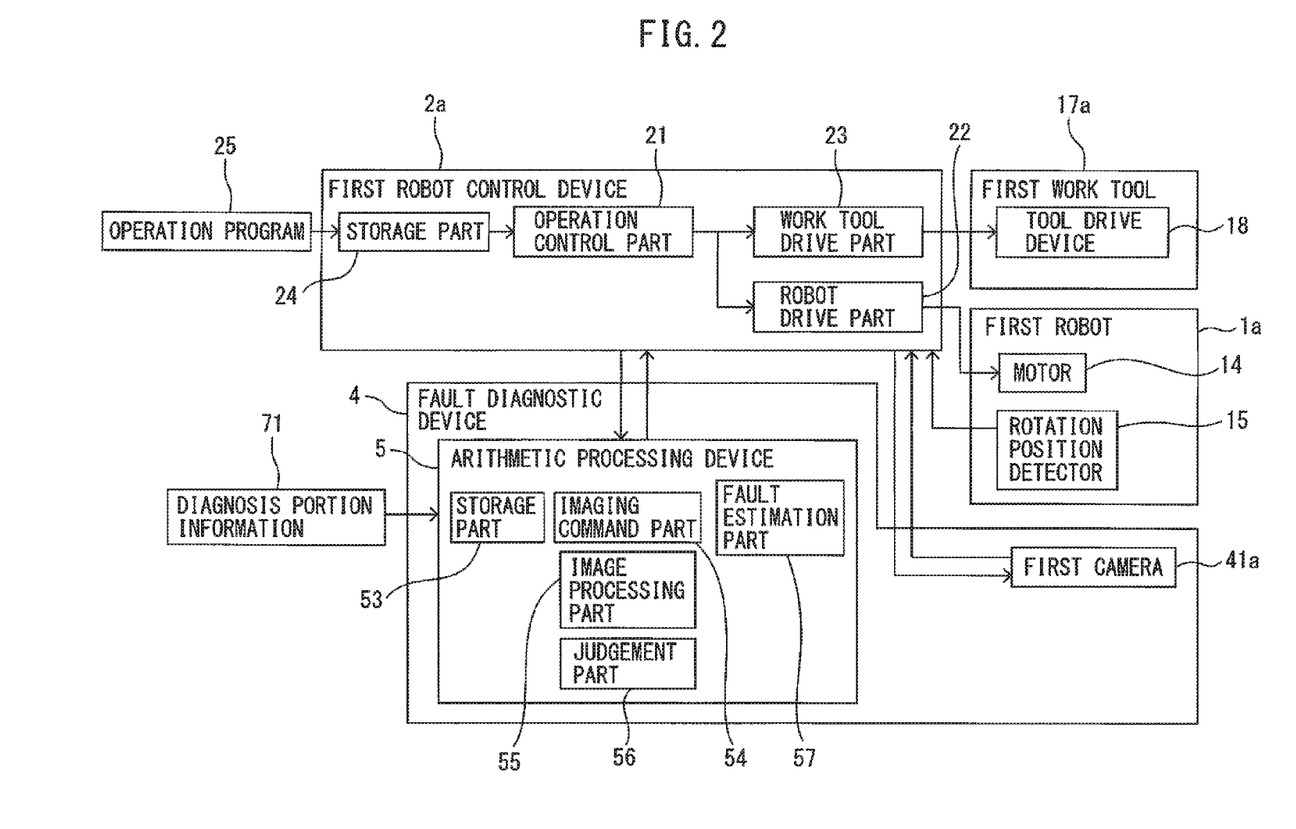
FIG. 2 is a block diagram of the first robot system in the embodiment.

FIG. 2 shows a block diagram of the robot system of the present embodiment. With reference to FIG. 1 and FIG. 2, the first manufacturing machine comprises the robot 1a and first robot control device 2a for controlling the work tool 17a. The robot control device 2a includes an arithmetic processing device including a CPU (Central Processing Unit), a RAM (Random Access Memory), a ROM (Read Only Memory), and the like connected with each other via a bus.

The robot control device 2a includes a storage part 24 for storing information related to control of the robot 1a and the work tool 17a. The robot control device 2a can drive the robot 1a and the work tool 17a in accordance with an operation program 25 input in advance. The operation program 25 is stored in the storage part 24.

The robot control device 2a includes an operation control part 21. The operation control part 21 transmits an operation command for driving the robot 1a and the work tool 17a. The operation control part 21 transmits the operation command for driving the robot 1a to a robot drive part 22. The robot drive part 22 includes an electrical circuit for driving a motor 14 of the robot 1a. The robot drive part 22 supplies electricity to the motor 14 for driving the arm and the like in accordance with the operation command. In addition, the operation control part 21 transmits an operation command for driving the work tool 17a to a work tool drive part 23. The work tool drive part 23 includes an electrical circuit for driving the tool drive device 18. The work tool drive part 23 supplies electricity to the tool drive device 18 in accordance with the operation command.

The robot 1a comprises a state detector for detecting an operation state of the robot 1a. The state detector of the present embodiment includes a rotation position detector 15 attached to the motor 14 of each driving axis. The rotation position detector 15 detects a rotation position when the motor 14 is driven. Information of the rotation position detected by the rotation position detector 15 is transmitted to the robot control device 2a. A rotational speed can be calculated on the basis of the rotation position of each driving axis. The robot control device 2a can detect a position and a posture of the robot 1a on the basis of the rotation position of each motor 14.

The fault diagnostic device 4 of the present embodiment comprises first camera 41a attached to a distal end of the robot 1a. The camera 41a of the present embodiment is fixed to a distal end of the wrist portion 16 of the robot 1a. A driving axis of the distal end of the robot 1a is arranged in the wrist portion 16. The camera 41a of the present embodiment moves together with the work tool 17a. When the work tool 17a rotates about the driving axis of the wrist portion 16, the camera 41a rotates.

The camera 41a is formed so as to change an imaging orientation in response that the robot 1a changes the position and the posture thereof. In other words, the camera 41a is arranged so as to change the position and the posture thereof by the driving of the robot 1a. The camera 41a of the present embodiment is arranged on the distal end of the wrist portion 16, however, may be fixed to the work tool 17a without being limited to this embodiment.

The camera 41a is connected to the first robot control device 2a. The camera 41a is controlled by the operation control part 21. The camera 41a of the present embodiment captures a two-dimensional image. As the camera 41a, an arbitrary imaging device can be adopted which can capture an image of the robot 1a or a peripheral device arranged around the robot 1a. For example, a three-dimensional camera may be adopted as the camera 41a.

The fault diagnostic device 4 comprises an arithmetic processing device 5 for judging the fault in a captured portion on the basis of the image captured by the camera 41a. The arithmetic processing device 5 includes a CPU, ROM, RAM, and the like.

In the first robot system, the fault diagnostic device 4 judges the fault in the robot 1a. In other words, the fault diagnostic device 4 judges the fault in a structural member of the robot 1a to which the camera 41a is attached. In the present invention, a portion of a device to be diagnosed by the fault diagnostic device 4 is referred to as a diagnosis portion. An arbitrary portion can be set as the diagnosis portion which can be captured by the camera 41*a* by changing the position and the posture of the robot 1*a*. Here, an upper surface 35*a* of a cover 35 of the motor 14 for driving the arm 12*a* is described as the diagnosis portion.

An operator inputs diagnosis portion information 71 to the arithmetic processing device 5. The diagnosis portion information 71 includes a name of the diagnosis portion of the robot 1*a*, the position and the posture of the robot 1*a* when the diagnosis portion is imaged, and an imaging condition of the camera 41*a*. The arithmetic processing device 5 includes a storage part 53 for storing information related to fault judgement. The diagnosis portion information 71 is stored in the storage part 53.

The diagnosis portion information 71 includes a reference image of the diagnosis portion when the diagnosis portion is normal. In the present embodiment, the reference image is created by actually capturing an image of the diagnosis portion when the robot 1*a* has no fault. When the reference image is captured, imaging is performed with setting the same position and posture of the robot 1*a* and the same imaging condition as imaging for fault judgement. In other words, the reference image is captured in the same state as a state in which the fault is judged. The reference image is not limited to this embodiment, and, for example, an image may be adopted which is created on the basis of three-dimensional shape data of the robot 1*a* output from a CAD (Computer Aided Design) device and the like.

The imaging condition of the camera 41*a* includes an imaging time at which the diagnosis portion is imaged in addition to a setting value of the camera 41*a* when imaging is performed. A normal imaging time in the present embodiment is set to a time when an accumulated operation time of the robot 1*a* reaches a predetermined time. In other words, fault judgement is performed at every predetermined operation time of the robot 1*a*. The imaging time is not limited to this embodiment, and an arbitrary timing can be specified. The imaging time may be individually set for each diagnosis portion.

The arithmetic processing device 5 includes an imaging command part 54 for transmitting a command for capturing the image of the diagnosis portion to the robot control device 2*a*. The imaging command part 54 detects the imaging time at which the predetermined diagnosis portion is imaged. In the diagnosis portion information 71, the position and the posture of the robot 1*a* are determined for imaging the selected diagnosis portion. Further, in the diagnosis portion information 71, the imaging condition of the camera 41*a* is determined for imaging the selected diagnosis portion. The imaging command part 54 transmits the command for changing the position and the posture of the robot 1*a* to the robot control device 2*a* on the basis of the diagnosis portion information 71. The robot control device 2*a* changes the position and the posture of the robot 1*a*.

Next, the imaging command part 54 transmits the command so as to capture the image of the diagnosis portion under the predetermined imaging condition to the robot control device 2*a* on the basis of the diagnosis portion information 71. The camera 41*a* captures the image of the diagnosis portion. In the example illustrated in FIG. 1, the robot 1*a* is controlled to the position and the posture at which the cover 35 of the motor of the joint portion 13 is imaged. The camera 41*a* captures the image of the cover 35 of the motor. The image captured by the camera 41*a* is transmitted to the arithmetic processing device 5 via the robot control device 2*a*.

The arithmetic processing device 5 includes an image processing part 55 for processing the image captured by the camera 41*a*. The image processing part 55 of the present embodiment divides the image captured by the camera 41*a* into a plurality of pixels and detects brightness of the pixels. The image processing part 55 judges a portion at which the brightness rapidly changes as a point on a contour of a component. Further, the points at which the brightness rapidly changes are connected to one another, and the contour of the component of the robot 1*a* is detected.

The arithmetic processing device 5 includes a judgement part 56 for judging whether or not the diagnosis portion has the fault on the basis of the image captured by the camera 41*a*. The judgement part 56 of the present embodiment judges whether or not the diagnosis portion has the fault on the basis of the contour of the component of the robot 1*a*.

Figure 3:
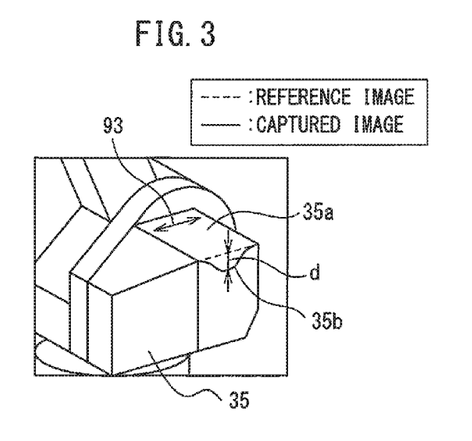
FIG. 3 illustrates a reference image and an image captured by a camera.

FIG. 3 shows a drawing in which the reference image and the image of the diagnosis portion captured by the camera are overlapped with each other. The reference image when the diagnosis portion is normal is stored in the storage part 53 in advance. In the present embodiment, the diagnosis portion is imaged at the position and the posture which are the same as the position and the posture of the robot 1*a* at which the reference image is captured. In addition, the camera 41*a* captures the image under the same condition as the imaging condition under which the reference image is captured. Therefore, when the diagnosis portion is normal, the reference image and the image captured by the camera 41*a* coincide with each other.

In the example illustrated in FIG. 3, the upper surface 35*a* of the cover 35 is partially dented and has a dented portion 35*b*. In other words, the cover 35 has an external damage. The judgement part 56 compares the image captured by the camera 41*a* with the reference image. When a difference in shapes exceeds a predetermined judgement amount, the judgement part 56 judges that the diagnosis portion has the fault. In the present embodiment, the judgement part 56 calculates a distance between contour lines in a predetermined direction. The judgement part 56 sets, for example, a vertical direction to the contour line of the reference image. The judgement part 56 calculates a maximum distance d from the contour line of the reference image to the contour line of the image captured by the camera 41*a*. The diagnosis portion information 71 includes a predetermined judgement value. When the maximum distance d is greater than the judgement value, the judgement part 56 judges that the diagnosis portion has the fault.

The judgement part 56 can perform analysis as above on each contour line. When the maximum distance d for at least one contour line in a plurality of the contour lines exceeds the judgement value, the judgement part 56 judges that the upper surface 35*a* of the cover 35 serving as the diagnosis portion has the fault. On the other hand, when the maximum distance d is equal to or less than the judgement value for all of the contour lines, the judgement part 56 judges that the diagnosis portion is normal with no fault.

When it is judged that the diagnosis portion has the fault, the arithmetic processing device 5 can perform an arbitrary control such as displaying the fault on a display part and the like. Alternatively, when it is judged that the diagnosis portion has the fault, the arithmetic processing device 5 can transmit a signal indicating occurrence of the fault to the robot control device 2*a*. Further, the robot control device 2*a* can perform an arbitrary control such as stopping driving of the robot and the like.

In the present embodiment, the judgement part 56 performs comparison on the contour line of the diagnosis portion in order to judge whether or not there is a difference in shapes exceeding the predetermined judgement amount. The control of the judgement part is not limited to this embodiment, and judgement can be made by an arbitrary control. For example, the judgement part can set an arbitrary direction on a single surface. The judgement part can calculate a brightness gradient in this direction. When a difference between a brightness gradient of the reference image and a brightness gradient of the image captured by the camera exceeds a predetermined judgement value, the judgement part can judge that there is a difference in shapes exceeding the predetermined judgement amount.

For example, in the example illustrated in FIG. 3, the judgement part 56 sets a direction of an arrow 93 on the upper surface 35a of the cover 35. Further, the judgement part 56 can calculate a change rate of pixel brightness in the direction of the arrow 93. When a difference between a change rate of pixel brightness in the reference image and a change rate of pixel brightness in the image captured by the camera 41a exceeds a judgement value, the judgement part 56 can judge that the upper surface 35a of the cover 35 is damaged.

As described above, the fault diagnostic device in the present embodiment can judge whether or not a predetermined diagnosis portion has the fault on the basis of the image captured by the camera. In particular, the fault diagnostic device 4 can judge whether or not an external damage is generated in the diagnosis portion.

The fault diagnostic device 4 of the present embodiment is formed so as to be capable of performing judgement in a plurality of diagnosis portions. The plurality of diagnosis portions are predetermined. For example, the arm 12a, a power cable, a communication line, a pipe, and the like can be set as the diagnosis portions. The storage part 53 stores reference images of the plurality of diagnosis portions. The imaging command part 54 transmits the imaging command so as to capture images of the plurality of diagnosis portions. The judgement part 56 can judge the fault in the plurality of diagnosis portions individually on the basis of the reference images of the plurality of diagnosis portions and the images of the plurality of diagnosis portions captured by the camera 41a. By performing the control, fault judgement can be performed in many portions which can be captured by the camera 41a.

For example, with reference to FIG. 1, by capturing the image by the camera 41a in a direction indicated by an arrow 91, the damage in an upper surface of the cover 35 can be judged. Further, by capturing the image by the camera 41a in a direction indicated by an arrow 92, the damage in a lower surface of the cover 35 can be judged.

Further, the camera 41a of the present embodiment can perform imaging by coming close to the diagnosis portion. For example, one surface of the component may be divided into a plurality of areas, and the diagnosis portions may be set thereto. The imaging command part 54 can transmit the command so as to capture the image of each divided diagnosis portion. The judgement part 56 can perform judgement for each divided area. Compared to the case in which the camera 41a performs imaging apart from the diagnosis portion, a small damage in the diagnosis portion can be judged.

The fault diagnostic device 4 may judge the fault using images captured from a plurality of predetermined directions with respect to the same diagnosis portion. The storage part 53 can store the reference images of the same diagnosis portion viewed from a plurality of directions. The diagnosis portion information 71 includes the position and the posture of the robot 1a corresponding to the diagnosis portion and an imaging direction. The diagnosis portion information 71 also includes the imaging condition of the camera 41a corresponding to the diagnosis portion and the imaging direction. The judgement part 56 can judge the fault in the diagnosis portion on the basis of the images of the diagnosis portion captured from the plurality of directions. By adopting this control, the fault judgement of the diagnosis portion can be performed more reliably.

With reference to FIG. 2, the arithmetic processing device 5 of the present embodiment includes a fault estimation part 57 for estimating a portion having a possibility of the fault on the basis of the operation state of the robot 1a. The operation state of the robot 1a can be detected on the basis of a signal of a detector attached to the robot 1a. For example, the fault estimation part 57 can detect that the motor 14 does not drive in response to the operation command by an output of the rotation position detector 15. In this case, the fault estimation part 57 can judge that there is a possibility that the motor 14 has the fault.

The operation state of the robot 1a can also be detected using the operation command generated by the operation control part 21. For example, the fault estimation part 57 detects the number of emergency stop signals transmitted from the operation control part 21. When the number of the emergency stops is large, a load is applied to a drive portion such as the joint portion. The fault estimation part 57 detects the number of the emergency stops in a predetermined time length. When the number of the emergency stops is greater than a predetermined judgement value, the fault estimation part 57 can judge that there is a possibility that the joint portion has the fault.

The fault estimation part 57 can detect feedback information, as the operation state, based on the output of the rotation position detector 15 attached to the motor 14 for driving the robot 1a. A feedback amount becomes greater as the rotation position of the motor 14 is distant from a position specified by the operation command. Therefore, when the feedback amount becomes greater than a predetermined judgement value, the fault estimation part 57 can judge that there is a possibility that the joint portion or the arm has the fault. As the feedback information, speed and acceleration may be adopted regardless of a position.

Further, a communication line for transmitting a signal of the rotation position detector attached to the motor may be corroded in some cases. When the communication line is corroded, a covering material may peel off. In this case, a noise may be generated in a position signal or a speed signal of the motor 14. The fault estimation part 57 detects that the feedback signal includes the noise. Then, the fault estimation part 57 can judge that there is a possibility that the communication line has the fault.

As described above, the fault estimation part 57 can estimate the portion having the possibility of the fault on the basis of the operation state. Further, by adopting the feedback information based on the output of the rotation position detector attached to the motor for driving the robot as the operation state of the robot 1a, possibilities of faults in the plurality of portions can be judged.

The diagnosis portion for diagnosing the portion which is judged to have the possibility of the fault is predetermined and stored in the storage part 53. The imaging command part 54 transmits the imaging command to the robot control device 2a so as to capture the image of the portion which has been judged to have the possibility of the fault. The imaging command includes the position and the posture of the robot 1a and the imaging condition when the camera 41a performs imaging. The image of diagnosis portion captured in response to the imaging command is transmitted to the arithmetic processing device 5 via the robot control device 2a. After the image processing part 55 processes the captured image, the judgement part 56 judges whether or not the portion which has been judged to have the possibility of the fault has the fault.

By performing the control for estimating an occurrence of the fault as described above, the operator can obtain whether or not the fault has occurred without confirming the occurrence of the fault by viewing the actual robot 1a. Further, the occurrence of the fault can be estimated before the component of the robot 1a is completely broken down. For example, deterioration of a cable can be detected early, and the operator can plan a repair.

Figure 4:
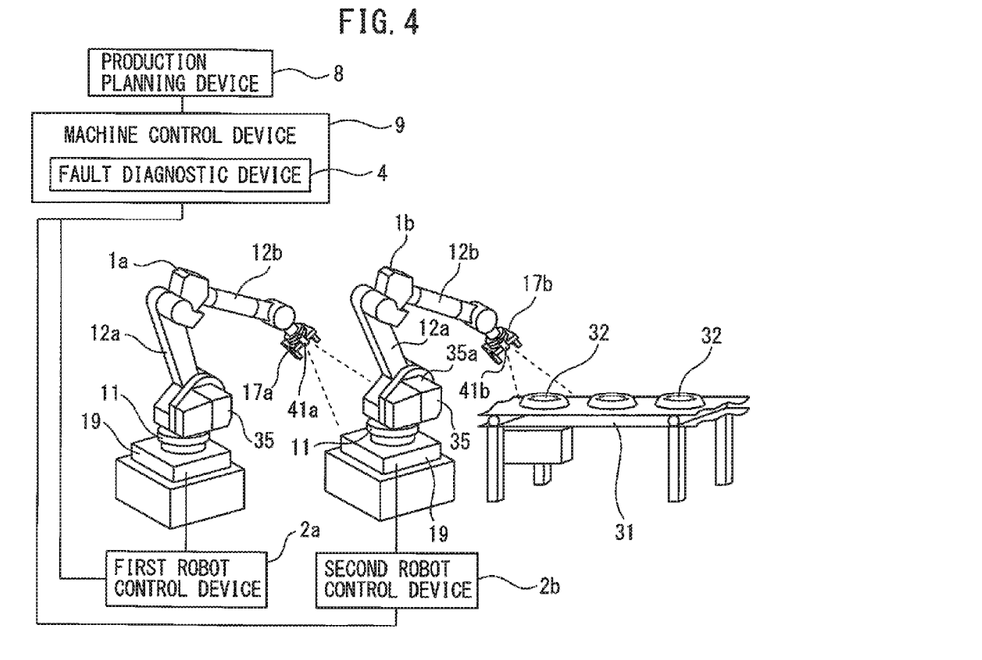
FIG. 4 is a schematic perspective view of second robot system in the embodiment.
Figure 5:
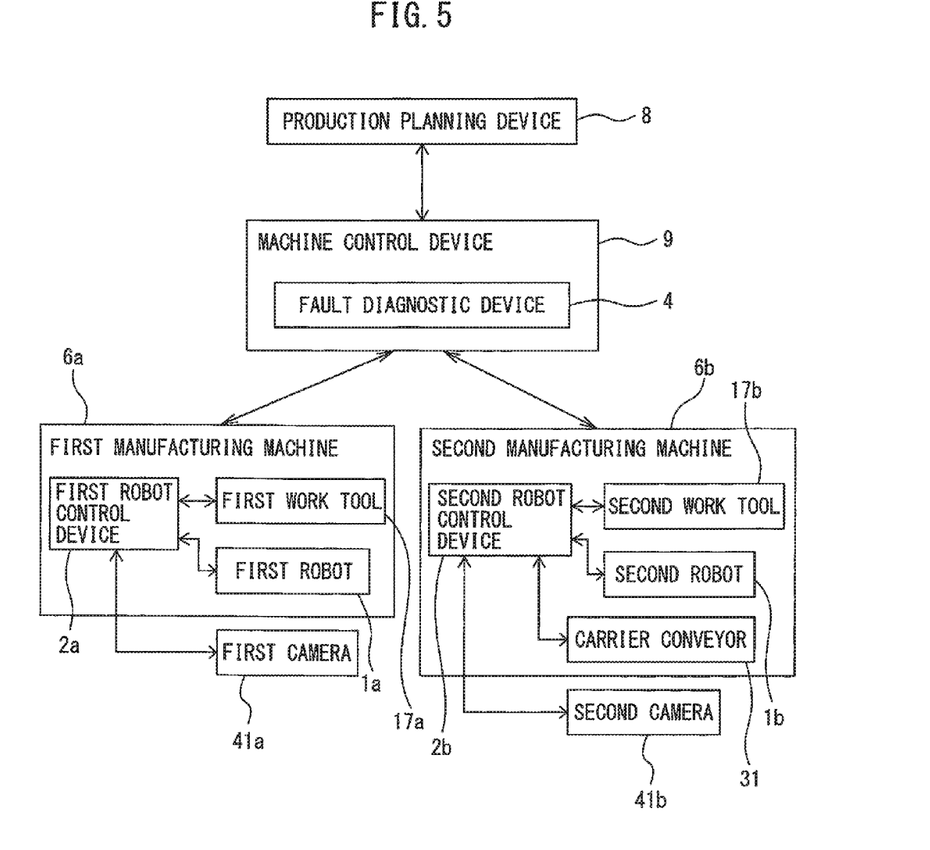
FIG. 5 is a block diagram of the second robot system in the embodiment.

FIG. 4 shows a schematic diagram of second robot system of the present embodiment. FIG. 5 shows a block diagram of the second robot system of the present embodiment. With reference to FIG. 4 and FIG. 5, the second robot system comprises second manufacturing machine 6b in addition to the first manufacturing machine 6a. The second robot system comprises a plurality of robots 1a and 1b.

The second manufacturing machine 6b comprises the second robot 1b, second robot control device 2b, second work tool 17b, and a carrier conveyor 31. The second robot 1b is similar to the first robot 1a in the first manufacturing machine 6a. The carrier conveyor 31 is formed so as to be capable of conveying a workpiece 32. The carrier conveyor 31 corresponds to the a peripheral device arranged around the second robot 1b.

The robots 1a and 1b are respectively provided with the cameras 41a and 41b. The second camera 41b of the present embodiment has a configuration similar to that of the first camera 41a. The second camera 41b is fixed to the distal end of the robot 1b or the work tool 17b.

The second robot control device 2b has a function similar to that of the first robot control device 2a. Further, the second camera 41b captures an image of the workpiece 32 conveyed by the carrier conveyor 31. The second robot control device 2b is formed so as to calculate a position of the workpiece 32 on the carrier conveyor 31 on the basis of the image of the workpiece 32 captured by the second camera 41b.

The second robot system comprises a machine control device 9 for controlling the manufacturing machines 6a and 6b. The machine control device 9 is formed so as to be capable of mutually communicating with the robot control devices 2a and 2b via a network. The machine control device 9 receives the operation states of the manufacturing machines 6a and 6b from the robot control devices 2a and 2b and transmits commands to the robot control devices 2a and 2b.

The second robot system comprises a production planning device 8 which is formed so as to be capable of communicating with the machine control device 9 via a network. The production planning device 8 is formed so as to perform management of processes in an entire factory and production management of products. The production planning device 8 functions as a management device for managing an entire production of products. For example, the production planning device 8 transmits a production plan of products to the machine control device 9. The machine control device 9 transmits an operation program to the robot control devices 2a and 2b in accordance with the production plan. The robot control devices 2a and 2b perform operations in accordance with the received operation program.

In the present embodiment, the manufacturing machines 6a and 6b are arranged in a factory for manufacturing the product. The machine control device 9 and the production planning device 8 may be arranged in a building different from the factory. For example, the machine control device 9 may be arranged in a different building in a manufacturing factory site. In this case, the machine control device 9 is connected to the robot control devices 2a and 2b via a network such as an intranet. Further, the production planning device 8 may be arranged in an office located in an area remote from the manufacturing factory. For example, the production planning device 8 is connected to the machine control device 9 via a network such as the Internet.

In the robot system, a manufacturing cell may be set which includes a plurality of manufacturing machines. The manufacturing cell can be separately set, for example, by manufacturing processes. The machine control device can be formed so as to control each manufacturing cell.

With reference to FIG. 2, FIG. 4, and FIG. 5, the machine control device 9 of the present embodiment includes the fault diagnostic device 4. The fault diagnostic device 4 comprises the second camera 41b. The fault diagnostic device 4 is formed so as to be capable of judging the fault in the first manufacturing machine 6a and the fault in the second manufacturing machine 6b. The diagnosis portion information 71 input to the arithmetic processing device 5 includes data regarding the first manufacturing machine 6a and data regarding the second manufacturing machine 6b.

Similar to the first manufacturing machine 6a, the fault in the component can be judged in the second manufacturing machine 6b by capturing the image of the component of the second robot 1b by the second camera 41b. The camera 41b for detecting a position of the workpiece 32 is provided in the second manufacturing machine 6b. Therefore, there is no need to newly add a camera for detecting the fault, and the camera 41b for detecting the position of the workpiece 32 can capture the image for detecting the fault.

Further, in the second manufacturing machine 6b, a fault in the carrier conveyor 31 can be judged. The diagnosis portion of the carrier conveyor 31 is predetermined. The diagnosis portion information 71 includes information of the diagnosis portion of the carrier conveyor 31. The storage part 53 stores the reference image of the diagnosis portion of the carrier conveyor 31 and the position and the posture of the robot 1b when the diagnosis portion is imaged. The second camera 41b captures an image of the diagnosis portion of the carrier conveyor 31. The arithmetic processing device 5 of the fault diagnostic device 4 judges whether or not the diagnosis portion of the carrier conveyor 31 has the fault on the basis of the reference image and the image captured by the second camera 41b.

As described above, the second robot system can judge the fault in the peripheral device arranged around the robot 1b. The peripheral device is not limited to the carrier conveyor, and an arbitrary device capable of capturing the image by the camera can be adopted. For example, the peripheral device includes a workpiece fixing device arranged near the robot. Further, the peripheral device includes a processing machine such as a machine tool arranged near the robot.

The peripheral device includes another robot arranged near the robot supporting the camera. In the second robot system, the second robot 1b is in proximity to the first robot 1a. Further, the first camera 41a supported by the first robot 1a can capture the image of the component of the second robot 1b. The fault diagnostic device 4 judges the fault in the component of the second robot 1b on the basis of the image captured by the first camera 41a.

The diagnosis portion information 71 includes the reference image corresponding to the image of the diagnosis portion of the second robot 1b captured by the first camera 41a. The diagnosis portion information 71 also includes the position and the posture of the first robot 1a and the position and the posture of the second robot 1b when the first camera 41a captures the image of the diagnosis portion of the second robot 1b. The fault diagnostic device 4 is formed so as to judge the fault in the component of the second robot 1b on the basis of the image captured by the first camera 41a.

As described above, the fault diagnostic device 4 of the second robot system can judge whether or not the diagnosis portion has the fault on the basis of the image captured by the first camera 41a and the image captured by the second camera 41b.

The second robot system of the present embodiment can capture images of the same diagnosis portion from directions different from each other by driving a plurality of robots 1a and 1b. The fault diagnostic device 4 can judge the fault on the basis of the captured images. The imaging command part 54 of the fault diagnostic device 4 transmits imaging commands to a plurality of robot control devices 2a and 2b so as to capture images of the same diagnosis portion. At that time, the imaging command part 54 transmits the imaging commands to a plurality of cameras 41a and 41b so as to capture images from directions different from each other.

With reference to FIG. 4, for example, the upper surface 35a of the cover 35 of the second robot 1b may be selected as the diagnosis portion in some cases. By changing the position and the posture of the second robot 1b, the second camera 41b can capture the image of the upper surface 35a of the cover 35. Further, by changing the position and the posture of the first robot 1a, the first camera 41a can capture the image of the upper surface 35a of the cover 35 in the second robot 1b. The imaging direction of the first camera 41a is different from the imaging direction of the second camera 41b.

The arithmetic processing device 5 acquires the images captured by the respective cameras 41a and 41b via the network. The judgement part 56 judges whether or not the diagnosis portion has the fault for each of the plurality of images. By performing this control, changes in a shape viewed from a plurality of directions can be detected with respect to the one diagnosis portion, and the fault in the diagnosis portion can be accurately detected.

In the second robot system, the arithmetic processing device 5 also includes the fault estimation part 57. In this regard, the structural member which has been judged to have the possibility of the fault by the fault estimation part 57 may not be captured by the camera supported by the robot including the structural member in some cases. The imaging command part 54 of the present embodiment selects the robot which can capture the image of the portion which has been judged to have the possibility of the fault by the fault estimation part 57. The imaging command part 54 transmits the command to the camera attached to the selected robot so as to perform imaging. The judgement part 56 judges whether or not the portion which has been judged to have the possibility of the fault has the fault on the basis of the captured image.

With reference to FIG. 4, for example, when the cover 35 of the robot 1b is judged to have the possibility of the fault, the image of the back surface of the cover 35 cannot be captured by the second camera 41b supported by the robot 1b in some cases. In this case, the imaging command part 54 selects the first camera 41a supported by the first robot 1a. The imaging command part 54 transmits the command so as to capture the image of the back surface of the cover 35 in the robot 1b. The arithmetic processing device 5 judges whether or not the back surface of the cover 35 is damaged on the basis of the captured image of the back surface of the cover 35.

By performing this control, the image of the diagnosis portion which cannot be captured by the camera supported by one robot can be captured by the camera supported by another robot. Accordingly, it is possible to enlarge an area in which occurrence of the fault can be judged.

When the fault in one diagnosis portion is judged, three or more cameras may capture images thereof. For example, there is a robot system in which third robot is arranged in addition to the first robot and the second robot. In this robot system, the diagnosis portion of the second robot may be captured using the camera supported by the first robot and the camera supported by the third robot, and the fault in the diagnosis portion may be judged.

In the second robot system, when the judgement part 56 of the arithmetic processing device 5 judges that the diagnosis portion has the fault, the arithmetic processing device 5 can transmit a signal indicating occurrence of the fault in the diagnosis portion to the production planning device 8. By performing this control, the operator who obtains information from the production planning device 8 can order the component which has broken down. Further, the operator can correct the production plan when the fault in the component affects the production plan of products.

Further, when the judgement part 56 of the arithmetic processing device 5 judges that the diagnosis portion has the fault, the arithmetic processing device 5 can transmits the image of the diagnosis portion to the production planning device 8 via the network. By performing this control, the operator operating the production planning device 8 can confirm a state of the fault. The operator can select or add the component to be ordered depending on the state of the fault.

In the robot system of the present embodiment, the fault diagnostic device and the robot control device are configured as different devices; however, the robot control device and the fault diagnostic device may be integrally formed. For example, the imaging command part, the image processing part, the judgement part, and the like may be arranged in the robot control device.

The robot of the present embodiment is the articulated robot; however, an arbitrary robot can be adopted without limiting to the present embodiment.

According to the present invention, the fault diagnostic device of the robot system can be provided which can detect damage on the outside of the robot and the device arranged around the robot.

The above-described embodiments can be appropriately combined. In each of the above-described drawings, the same or the corresponding portions are denoted by the same reference numerals. The above-described embodiments are merely examples and not intended to limit the invention. Further, the embodiments include modifications thereof within the scope of the claims.

The invention claimed is:

1. A fault diagnostic device of a robot system including a plurality of robots, the fault diagnostic device comprising:
    cameras fixed to at least two parts among
        distal ends of the robots, and
        work tools attached to the robots; and an arithmetic processing device configured to judge a fault in at least one of the robots supporting the cameras and a peripheral device around the robots, based on images of a diagnosis portion captured by the cameras, wherein the arithmetic processing device includes a storage storing information of the diagnosis portion,
    positions and postures of the robots when the diagnosis portion is imaged, and
    reference images when the diagnosis portion does not have the fault, the arithmetic processing device is connected to control devices of the robots via a network, and is configured to acquire the images of the diagnosis portion captured by the cameras via the network, the arithmetic processing device is configured to transmit imaging commands to the control devices of the plurality of the robots so as to cause the cameras to capture the images of the diagnosis portion from directions different from each other after changing the positions and the postures of the robots based on the information of the diagnosis portion, and the arithmetic processing device is configured to judge whether or not the diagnosis portion has the fault based on the images of the diagnosis portion captured by the cameras, by
    comparing the images of the diagnosis portion captured by the cameras with the reference images, and
    judging that the diagnosis portion has the fault when there is a difference of shapes exceeding a predetermined judgement amount.

2. The fault diagnostic device according to claim 1, wherein
the storage stores the reference images of a plurality of diagnosis portions, and
the arithmetic processing device is configured to
    transmit the imaging commands so as to cause the cameras to capture images of the plurality of diagnosis portions, and
    judge whether or not the plurality of diagnosis portions has the fault based on the reference images of the plurality of diagnosis portions and the images of the plurality of diagnosis portions captured by the cameras.

3. The fault diagnostic device according to claim 1, wherein
the robot system comprises a management device connected to the arithmetic processing device, and
when the arithmetic processing device judges that the diagnosis portion has the fault, the arithmetic processing device is configured to transmit a signal indicating occurrence of the fault in the diagnosis portion to the management device.

4. The fault diagnostic device according to claim 3, wherein, when the arithmetic processing device judges that the diagnosis portion has the fault, the arithmetic processing device is configured to transmit the images of the diagnosis portion to the management device via the network.

5. The fault diagnostic device according to claim 1, wherein
the arithmetic processing device is further configured to
    judge that the diagnosis portion has a possibility of the fault based on an operation state of at least one of the plurality of robots,
    transmit the imaging commands so as to cause the cameras to capture the images of the diagnosis portion which has been judged to have the possibility of the fault, and
    judge whether or not the diagnosis portion which has been judged to have the possibility of the fault has the fault.

6. The fault diagnostic device according to claim 1, wherein
the arithmetic processing device is further configured to
    judge that the diagnosis portion has a possibility of the fault based on an operation state of at least one of the plurality of robots,
    select, among the plurality of robots, one or more robots for capturing the images of the diagnosis portion which has been judged to have the possibility of the fault,
    transmit the imaging commands so as to cause the cameras attached to the selected robots to capture the images of the diagnosis portion which has been judged to have the possibility of the fault, and
    judge whether or not the diagnosis portion which has been judged to have the possibility of the fault has the fault.

7. The fault diagnostic device according to claim 5, wherein the operation state includes feedback information based on an output of a rotation position detector attached to a motor for driving one of the plurality of robots.

* * * * *